United States Patent [19]

Krall et al.

[11] Patent Number: 5,516,480
[45] Date of Patent: May 14, 1996

[54] BACTERICIDAL AND/OR FUNGICIDAL PLASTIC PARTS FOR USE IN THE MEDICAL FIELD

[75] Inventors: Theodor Krall, Rosenau 7a, 6600 Lechaschau, Austria; J. Peter Guggenbichler, Bamberg; Monika Girisch, Weiden, both of Germany

[73] Assignees: Peter Guggenbichler, Bamberg, Germany; Theodor Krall, Lechaschau, Austria

[21] Appl. No.: 381,829

[22] PCT Filed: Aug. 12, 1993

[86] PCT No.: PCT/DE93/00726

§ 371 Date: Mar. 31, 1995

§ 102(e) Date: Mar. 31, 1995

[87] PCT Pub. No.: WO94/04202

PCT Pub. Date: Mar. 3, 1994

[30] Foreign Application Priority Data

Aug. 13, 1992 [DE] Germany .................... 42 26 810.9

[51] Int. Cl.[6] .............................. B29C 71/00; A61L 29/00
[52] U.S. Cl. ..................... 264/343; 264/345; 427/2.24; 604/265
[58] Field of Search ...................... 264/341, 232, 264/344, 343, 345, 340, 233; 604/265; 427/2.24

[56] References Cited

U.S. PATENT DOCUMENTS

| | | | |
|---|---|---|---|
| 3,524,447 | 8/1970 | Evans et al. | 264/341 |
| 3,881,026 | 4/1975 | Shepherd et al. | 426/590 |
| 4,054,139 | 10/1977 | Crossley | 128/260 |
| 4,569,673 | 2/1986 | Tesi | 604/265 |
| 4,612,337 | 9/1986 | Fox, Jr. et al. | 523/113 |
| 4,917,686 | 4/1990 | Bayston et al. | 604/265 |
| 4,973,320 | 11/1990 | Brenner et al. | 604/265 |
| 5,019,096 | 5/1991 | Fox et al. | 604/265 |
| 5,322,659 | 6/1994 | Walder et al. | 264/232 |
| 5,344,411 | 9/1994 | Domb et al. | 604/265 |

FOREIGN PATENT DOCUMENTS

| | | |
|---|---|---|
| 0301717 | 2/1989 | European Pat. Off. |
| 0550875 | 7/1993 | European Pat. Off. |
| 2209582 | 7/1974 | France . |
| 1939687 | 3/1970 | Germany . |
| 3725728 | 2/1989 | Germany . |
| 8703495 | 6/1987 | WIPO . |
| 8904682 | 6/1989 | WIPO . |

OTHER PUBLICATIONS

Database WPI, Week 9241, Derwent Publications Ltd., London, GB; AN 92–337629 & JP,A, 4 243 908 (Rasa Kogyo KK) Sep. 1992.

*Primary Examiner*—Jeffery R. Thurlow
*Attorney, Agent, or Firm*—Panitch Schwarze Jacobs & Nadel

[57] ABSTRACT

A process is provided for producing a plastic part that cannot be colonized by germs and/or fungi. The process includes the step of sequentially treating the plastic part with a swelling agent to provide a swollen plastic part, and then treating the swollen plastic part with a solution of a water-insoluble compound containing a bactericidal and/or fungicidal metal, where the solution has a bactericidally and/or fungicidally effective concentration of the insoluble compound.

13 Claims, No Drawings

BACTERICIDAL AND/OR FUNGICIDAL PLASTIC PARTS FOR USE IN THE MEDICAL FIELD

FIELD OF THE INVENTION

This invention relates to plastics parts, particularly for use in the medical field, which do not permit a colonisation by germs and/or fungi for an extended time period. This time-extension is such that the result is a clearly reduced risk for the patients of an infection with pathogens during the entire application.

BACKGROUND OF THE INVENTION

According to the present state of the art, a number of products containing plastics for use in the medical field are commercially available. In many of these products, an essential component is a tube with one or several lumen/lumina. These products are sterilized, e.g. with ethylene oxide, and commercially available in air-tight packaging.

Once taken out of the packaging, however, they are no longer sterile. Impermeable and smooth materials are preferably used for such products in order to minimize the colonisation by bacteria and fungi. However, particularly when used for a longer period of time or even for long-term application, these products can be subject to a colonisation by germs, which finally do harm to the patient using these products.

Scientists trying to add small amounts of antibiotics, also in combination with metal-containing compounds, or to apply antibiotics-containing coatings to products of the above-described type have obviously not been successful, at least up to now, e.g. U.S. Pat. No. 4,612,337. The main risk in this context is the development of resistance to antibiotics due to the long-term release of low amounts of antibiotics.

The anti-microbial properties of silver are also of importance. Even traces of silver and its salts have bacteriostatic and bactericidal effects. This disinfecting effect is caused by the "oligodynamy" phenomenon found by C. von Naegli in 1893, which is supposedly based on the dissolving silver ions.

Also the "Composition for decontaminating liquids containing germs" disclosed in German patent DE-900 000 works on to this principle. The composition contains a complex salt consisting of a heavy metal salt with specific oligodynamic effect (e.g. Ag) and a soluble halide capable of forming a complex salt, a readily soluble salt of a metal or an organic base.

DE-A-37 25 728, EP-A-0 301 717 and U.S. Pat. No. 4,054,139 disclose medical polymer materials, in which silver (compounds) is/are mechanically introduced into the material. A sufficiently long-lasting sterility cannot be achieved with these materials, either. Nor did trying to treat such products with a strongly bactericidal silver nitrate in order to obtain sterility for a long period of time lead to positive results. Due to its solubility in water, the silver nitrate was probably simply washed out.

The bactericidal and/or fungicidal effects of other metals are also well known. For instance those of copper, which is described in EP-A-0 116 865 and which particularly exhibits also a strong fungicidal effect, as well as those of gold, zinc and cerium, which are also disclosed in U.S. Pat. No. 4,612,337.

However, so far researchers have not succeeded in obtaining satisfying results in impregnating plastics parts with these metals.

Besides, the bactericidal and/or fungicidal effects of these metals are not sufficient to satisfy all practical requirements. On the contrary, there is a need for means based on such metals in which, however, the bactericidal and/or fungicidal effect of these metals is increased.

DESCRIPTION OF THE PREFERRED EMBODIMENTS

The object underlying this invention is to provide a process making it possible to produce plastics parts, preferably for use in the medical field, which exhibit a very high bactericidal and/or fungicidal effect even after long periods of non-sterile application to humans or animals.

This problem is solved by a process for producing plastics parts which cannot be colonised by germs characterized in that the plastics is pre-treated with a swelling agent and the obtained swollen plastics is treated with a solution of a compound containing a bactericidal and/or fungicidal metal.

The subject-matter of the invention includes plastics parts produced according to this process.

The compounds containing a bactericidal and/or fungicidal metal are preferably compounds that are non-soluble in water since otherwise there would be an increased risk of the bactericidal and/or fungicidal metal being washed out of the plastics part by body fluids during the application to humans or animals and thus perhaps reducing the long-term bactericidal and/or fungicidal effects of the plastics part.

It is also preferred that the metal-containing compound is an inorganic metal salt. The metal is preferably silver, copper, gold, zinc or cerium. Of these metals, silver and copper, and especially silver are especially preferred. Excellent results in the production of plastics parts which cannot be colonised by germs can be achieved particularly with silver halides, such as silver chloride, and copper (I) halides, such as copper (I) iodide. It is also possible to use mixtures of compounds with different metals. In this respect, a mixture of copper (I) iodide and silver chloride is preferred.

The polymer compounds suitable for the plastics part that cannot be colonised by germs are the plastics generally used in the medical field. These are in particular polyethylene, polypropylene, branched polysiloxanes, polyurethanes, (meth)acrylate polymers, cellulose and cellulose derivatives, polycarbonates, ABS, tetrafluorethylene polymers and polyethylene terephtalates, as well as the corresponding copolymers. Especially preferred are polyethylene and polypropylene as well as polyethylene-polypropylene copolymers.

The plastics parts are preferably used in devices which are in any way implanted into the human or animal body or applied thereto. Such products include shunts, cannulas, dressings, endotracheal tubes, percutaneous devices, intraocular lenses, contact lenses, sutures and any desired other implants that can be made of plastics; however, particularly catheters of any kind.

In a particularly preferred embodiment, the plastics swollen by means of a swelling agent is treated with a solution containing a bactericidal and/or fungicidal metal without drying first with the compound containing a bactericidal and/or fungicidal metal being more readily soluble in the solvent it was dissolved in than in the swelling agent used for swelling the plastics. In addition, the solvent should be mixable with the swelling agent. The advantage of this embodiment is that a concentration gradient develops in the swollen plastics between the better solvent for the compound containing a bactericidal and/or fungicidal metal and the worse solvent for this compound. In the better solvent, the metal-containing compound diffuses at first into the swollen plastics part until the portion of worse solvent predominates and the compound precipitates in the plastics part. Since the thus formed concentration gradient in the solution mixture is neutralized by diffusion, it is possible to achieve a higher concentration of bactericidal and/or fungicidal metal in the plastics part. Since, in addition, the distribution gradient between better solvent for the compound and worse solvent for the compound continually changes, a special distribution (gradient) of the bactericidal and/or fungicidal metal is achieved in the plastics part, which—in practice—has proven to be rather effective in preventing germs from colonising this plastics part even when applied to humans and animals for longer periods and in contact with body fluids. Interaction between the plastics and the metal compound can also play a role in the development of the distribution of the silver compound within the plastics.

In a different embodiment, a suitable plastics part (e.g. a tube) is treated with swelling agent on one side and with the solution containing a bactericidal/fungicidal metal on the other side.

It is also preferred that the compound containing a bactericidal and/or fungicidal metal is dissolved in a solvent that can combine with this metal to form a stable complex. The reasons are that firstly, it was found that the use of complexed metals also leads to a particularly advantageous distribution profile of the compound containing a bactericidal and/or fungicidal metal in the plastics part; and secondly, it has been found that the bactericidal and/or fungicidal effectiveness of individual metals can be increased by complexing them in a solvent.

It was also found that in the case of a solution of a metal-containing (particularly a silver-containing) compound in an alkanol amine, the metal (silver) alkanol amine complex that is formed exhibits clearly improved bactericidal and/or fungicidal effectiveness when compared to a solution of a metal- (silver-) containing compound in a non-complexing solvent.

However, also other applications in the medical field are possible for these expressedly strongly bactericidally effective means where especially high bactericidal and/or fungicidal effectiveness is of importance. In particular, the means of this invention are advantageous for fighting gram-positive or gram-negative bacteria such as *S. aureus, S. faecalis*, group B. streptococci, *E. coli*, Klebsiella, Proteus, Salmonella, Enterobacter, Serratia, *P. aeruginosa*, Acinetobacter.

In view of the above, the more preferred swelling agents are lower alcohols with no more than 10 carbon atoms, such as methanol, ethanol, propanol, isopropanol, and the four isomeric butanols, especially ethanol, as well as lower ketones usually used as solvents, such as methyl ethyl ketone or acetone, especially acetone. Chlorinated hydrocarbons are not preferred but can also be used if so desired by the person skilled in the art.

The preferred solvents are organic amines, especially alkanol amines with up to 10 carbons and, above all, ethanol amine. Also diethanol amine and triethanol amine are preferably used.

Solutions of the metal salt that are saturated at room temperature are preferably produced in the solvent.

This results in one of the preferred embodiments being a solution of an inorganic silver or copper (I) salt, preferably silver chloride and/or copper (I) iodide in an alkanol amine, preferably ethanol amine, which is used together with a swelling agent with the swelling agent being preferably ethanol and/or acetone.

It is most preferred to execute the process as follows:

At first, the silver or copper (I) salt is dissolved in ethanol amine at high concentration (i.e. close to the saturation point) and the plastics is treated with a swelling agent which can be mixed with the above-mentioned solvent for the silver or copper (I) salt, but itself hardly dissolves the silver or copper (I) salt (e.g. acetone or ethanol). Upon bringing the swollen plastics into contact with the silver salt or the copper (I) salt solution, also the silver or copper (I) salt diffuses into the plastics and thus precipitates from the solvent mixture. By subsequent drying, the silver or copper salt can be stored permanently in the plastics. This process can be carried out already with the preproduct, that is the plastics granulates.

The example illustrates the invention. If not mentioned otherwise, in the following the impregnation was effected with a solution of silver chloride in ethanol amine at room temperature.

EXAMPLE

Treatment of a tube (catheter) with
AgCl/H$_2$NCH$_2$CH$_2$OH

A particularly effective procedure was tested in that an HDPE tube was kept in acetone for one day and thus at least was swollen up within what is possible. PU tubes are sufficiently swollen within 2 hours and can then be further processed. Then it was quickly emptied and filled with a solution of silver chloride in ethanol amine. The acetone located in the walls of the tube could evaporate to the exterior. The thus treated tube was then once again treated completely with the silver salt solution in order to obtain a sufficiently effective silver-chloride coating on the outside too. The total absorption of silver chloride amounted to 0.5% of the weight of the tube.

Preparation of the germ suspension for testing the germ colonisation

As the germ suspension, a 5% glucose solution was inoculated with *Staphylococcus epidermidis* in an order of magnitude of two calibrated loops of *Staphylococcus epidermidis* from the blood agar plate per one liter glucose. This makes about 500,000 germs/ml.

Since glucose has a slightly bactericidal effect, the germ suspension was re-inoculated daily to grant that the same amount of germs was present. The colonisation by germs and the inoculum density were checked regularly.

The germ was inoculated into a sterile cryocontainer for storage and stored at −60° C. Such a cryocontainer contains several granules which completely bind microorganisms. When the germ was needed, a new culture was prepared by rolling one granule on a blood agar plate and then incubating the culture for 24 hours at 37° C.

Testing the germ colonisation

The catheters were first sterilized with ethylene oxide and then flushed with the above-described germ suspension at a flow rate of 10 ml/hour. Initially, the flow rate was limited by means of a peristaltic pump, later by means of a helix control system in order to test several catheters simultaneously.

Every six to eight hours, later every twelve hours, the catheters were flushed with 100 ml of a 0.9% saline solution via a three-way cock and then an approx. 1 cm long piece of the catheter was cut off using sterile scissors. This catheter piece was now immersed in 2 ml Todd Hewitt Broth and incubated at 37° C. for at least 48 hours.

If the nutrient broth clouded, the catheters were considered contaminated. The catheters were flushed with the germ suspension until contaminated or, if the sterility was maintained, for 200 hours.

The anti-microbial effect of the silver-impregnated catheters was compared to the germ colonisation of untreated control catheters in a double-blind process.

Histocompatibility

In this experiment, the influence of different catheter materials on the vitality of phytohemagglutinine-stimulated lymphocytes was determined.

After measuring the lymphocyte cultures in the photo meter at an optical density of 550 nm, the percentage of lymphocytes still alive could be determined.

Thrombogenity test

For every thrombogenity test one silver-impregnated catheter made of pellethan was perfused with fresh blood containing 2.5 ml ACD solution per 10 ml whole blood for eight hours. The flow rate through the catheter amounted to 5.5 ml per hour. In two-hour intervals, 3.5 ml of the starting blood and 3.5 ml of the blood that had passed the catheter were taken and tested for the coagulation values Quick's, PTT, TT, total concentration of fibrinogen and thrombin time.

| Results of anti-microbial effect |
|---|
| Polyethylene/polypropylene (PE/PP): |
| untreated control catheter: contaminated after 18 hours silver-impregnated catheter (swelling in acetone): sterile for 168 hours* |
| Polyurethane (PU): |
| a) PU I (Cavafix ® produced from Pellethane ®): | untreated control catheter: contaminated after 24 hours
silver-impregnated catheter:

| swelling agent | impregnation inside (min) | impregnation outside (min) | result |
|---|---|---|---|
| isopropanol | 195 | 120 | sterile after 350 hrs.* |
| ethanol | 177 | 120 | sterile after 350 hrs.* |
| ethanol | 185 | none | sterile after 350 hrs.* |
| ethanol | 198, 120 | none | sterile after 350 hrs.* |
| acetone | 90 | 120 | contaminated after 192 hrs. |
| ethanol amine | 155 | 120 | contaminated after 192 hrs. |
| no swelling | 171 | 120 | contaminated after 168 hrs. |
| ethanol | none | 184 | contaminated after 144 hrs. |
| ethanol | none | 151, 120 | contaminated after 144 hrs. | b) PU II (Tecothane ® 1095A,4-Liner):

untreated control catheter: contaminated after 55 hours
silver-impregnated catheter (swelling with acetone or ethanol, Ag solution saturated or 6%): sterile for 168 hours*

| Results of anti-microbial effect |
|---|
| c) PU III (Certofix ® produced from Tecoflex ® EG 93 A B20): |
| untreated control catheter: contaminated after 15 hours silver-impregnated catheter (swelling with acetone): sterile for 168 hrs.* |
| d) PU IV (Elastollan ® 1195 A 10L + 25% BaSO4): |
| untreated control catheter: contaminated after 5 hours silver-impregnated catheter (swelling with acetone): still sterile after 286 hours* |
| Silicone: |
| untreated control catheter: contaminated after 2 hours silver-impregnated catheter (swelling with acetone): still sterile after more than 200 hours* |

*The experiment was concluded since the sample material for testing the sterility was used up.

In those cases when a colonisation took place during the duration of the experiment, a reduction of colonisation density could frequently be observed in the further course of the experiment so that, in the course of time, the catheter became "more sterile" again. This effect is also due to the special distribution of the metal-containing compound in the catheter.

The accompanying control experiments also showed that even catheters that were only treated with the amines used for complexing (e.g. ethanol amine), i.e. without a silver compound, exhibited a slightly bactericidal effect.

Results of the histocompatibility tests

Results of the histocompatibility tests in lymphocyte cultures:

|  | after 48 hours | | after 72 hours | |
|---|---|---|---|---|
|  | OD 550 | vitality (%) | OD 550 | vitality (%) |
| Certofix | 0.068 | 40,96 | 0.065 | 25.59 |
| Certofix* | 0.052 | 31.33 | 0.041 | 16.14 |
| Cavafix | 0.166 | 100 | 0.175 | 68.90 |
| Cavafix* | 0.145 | 87.35 | 0.136 | 53.54 |
| Tecothane | 0.119 | 71.69 | 0.134 | 52.76 |
| Tecothane* | 0.106 | 63.86 | 0.068 | 26.77 |
| Ellastollan | 0.075 | 45.18 | 0.095 | 37.40 |
| Ellastollan* | 0.055 | 33.13 | 0.019 | 7.48 |
| PHA-L. | 0.166 | 100 | 0.254 | 100 |

*silver-impregnated catheter

The results of these experiments in lymphocyte cultures show that impregnating the catheters with silver only results in a slight reduction of vitality of PHA-stimulated lymphocytes in comparison to untreated catheters.

Catheters Cavafix and Tecothane exhibit the best biological compatibility.

However, it is remarkable that even untreated Certofix and Ellastolan catheters resulted in a relatively high rate of lymphocyte decay.

| Results of the thrombogenity test | | | | |
|---|---|---|---|---|
| | Starting Blood: | | | |
| O value: | Hb | 15.5 | Quick | 102 |
| | Ery | 5.27 | PTT | 32.4 |
| | Leuk | 6.6 | TT | 16.9 |
| | Hkt | 47.5 | Fibr | 235 |

-continued

Results of the thrombogenity test

| | MCV | 90 | Thco | 17.9 |
|---|---|---|---|---|
| | MCHC | 33 | | |
| | Thr | 217 | | |

| Starting blood | | Blood from the catheter | |
|---|---|---|---|
| after 2 hours: | | | |
| Quick | 26 | Quick | 32 |
| PTT | >120 | PTT | >120 |
| TT | 23.6 | TT | 22.5 |
| Fibr | 153 | Fibr | 155 |
| Thco | 19.9 | Thco | 19.7 |
| after 4 hours: | | | |
| Quick | 28 | Quick | 34 |
| PTT | >120 | PTT | >120 |
| TT | 22.8 | TT | 22.9 |
| Fibr | 139 | Fibr | 159 |
| Thco | 19.0 | Thco | 19.3 |
| after 6 hours: | | | |
| Quick | 21 | Quick | 32 |
| PTT | >120 | PTT | >120 |
| TT | 23.8 | TT | 22.9 |
| Fibr | 149 | Fibr | 154 |
| Thco | 20.4 | Thco | 19.6 |
| after 8 hours: | | | |
| Quick | 29 | Quick | 30 |
| PTT | >120 | PTT | >120 |
| TT | 24.1 | TT | 24.7 |
| Fibr | 150 | Fibr | 160 |
| Thco | 18.3 | Thco | 18.4 |
| Quick: | thromboplastine time according to Quick | | |
| PTT: | partial thromboplastin time | | |
| TT: | thrombin time | | |
| Fibr: | total concentration of fibrinogen | | |
| Thco: | thrombin coagulase time | | | the results of the thrombogenity test show that the thrombin coagulase time and the concentration of fibrinogen remained constant over the entire time of the experiment, so did essentially the number of thrombocytes. In both blood samples the Quick value was around 20–30% after 2 hours but then did not decrease any more. The thrombin time was mostly around 20 seconds and the partial thromboplastin time was always above 120 seconds.

Since the values are always almost identical in both blood samples, it can be concluded that the silver-impregnation of catheters does not effect the coagulation and has no thrombogenic effect.

Of course, this process regarding the introduction of the silver chloride can be influenced with respect to various parameters and can thus be improved in economical terms too. However, basically it presents the opportunity to produce the products of this invention such that they represent a considerable progress for the field of medicine with respect to the reduction of the risk of doing harm to the patients by infiltrating germs when applied.

We claim:

1. A process for producing a plastic part that cannot be colonized by germs and/or fungi, comprising the step of sequentially treating the plastic part with a swelling agent to provide a swollen plastic part, and treating the swollen plastic part with a solution of a water-insoluble compound containing a bactericidal and/or fungicidal metal, said solution having a bactericidally and/or fungicidally effective concentration of said compound.

2. The process of claim 1, wherein the compound containing a bactericidal and/or fungicidal metal is an inorganic metal salt.

3. The process of claim 1, wherein the bactericidal and/or fungicidal metal is silver, copper, gold, zinc or cerium.

4. The process of claim 1, wherein the solvent for the compound containing a bactericidal and/or fungicidal metal can complex the metal.

5. The process of claim 1, wherein the swollen plastic is treated with a solution of a compound containing a bactericidal and/or fungicidal metal without being dried first, and wherein the compound containing a bactericidal and/or fungicidal metal is not as readily soluble in the swelling agent for the plastic as in the solvent in which it is dissolved.

6. The process of claim 1 wherein the swelling agent is acetone or ethanol.

7. The process of claim 1 wherein the solvent contains an organic amine or ammonia.

8. The process of claim 7 wherein the organic amine is an alkanolamine.

9. The process of claim 8 wherein the alkanolamine is ethanolamine.

10. The process of claim 1 wherein the compound containing a bactericidal and/or fungicidal metal is silver chloride and the solvent for this compound is ethanolamine.

11. The process of claim 1 wherein the plastic part contains polyethylene, polypropylene, polyurethane, silicone, alone or in combination.

12. The process of claim 1 wherein the plastic part is a preproduct for medical devices.

13. A plastic part prepared according to the process of claim 1 that cannot be colonized by germs.

* * * * *